United States Patent
Fuhs et al.

(10) Patent No.: US 9,079,020 B2
(45) Date of Patent: Jul. 14, 2015

(54) TERMINAL RING CONFIGURATION TO PREVENT IMPROPER IS4 LEAD CONNECTOR ELECTRICAL CONTACT WITH DF4 CONNECTOR PORT

(71) Applicant: Cardiac Pacemakers, Inc., St. Paul, MN (US)

(72) Inventors: Christopher A. Fuhs, Roseville, MN (US); Adam J. Rivard, Blaine, MN (US); Kyle Hoecke, Lino Lakes, MN (US); Daniel J. Cooke, Roseville, MN (US); Bryan A. Clark, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 12 days.

(21) Appl. No.: 14/052,915

(22) Filed: Oct. 14, 2013

(65) Prior Publication Data

US 2014/0107754 A1 Apr. 17, 2014

Related U.S. Application Data

(60) Provisional application No. 61/715,046, filed on Oct. 17, 2012.

(51) Int. Cl.
| | |
|---|---|
| *A61N 1/18* | (2006.01) |
| *A61N 1/05* | (2006.01) |
| *A61N 1/375* | (2006.01) |
| *H01R 24/58* | (2011.01) |

(Continued)

(52) U.S. Cl.
CPC .............. *A61N 1/059* (2013.01); *A61N 1/3752* (2013.01); *A61N 1/3968* (2013.01); *H01R 13/642* (2013.01); *H01R 24/58* (2013.01); *A61N 1/3925* (2013.01); *A61N 1/3962* (2013.01); *H01R 13/17* (2013.01); *H01R 2201/12* (2013.01)

(58) Field of Classification Search
CPC ....... A61N 1/056; A61N 1/3752; A61N 1/05; A61N 1/0565; A61N 1/375; A61N 1/0587; A61B 18/1492; A61B 2017/003; H01R 2201/12; H01R 2107/00; H01R 24/58; H01R 4/4818
USPC ............. 607/37, 38, 115, 116, 119, 122, 123, 607/126, 133
See application file for complete search history.

(56) References Cited

U.S. PATENT DOCUMENTS

| | | |
|---|---|---|
| 5,769,671 A | 6/1998 | Lim |
| 6,878,013 B1 | 4/2005 | Behan |

(Continued)

FOREIGN PATENT DOCUMENTS

| | | |
|---|---|---|
| WO | WO2006012033 A2 | 2/2006 |
| WO | WO2010051495 A1 | 5/2010 |

OTHER PUBLICATIONS

International Search Report and Written Opinion issued in PCT/US2013/064789, mailed Dec. 20, 2013, 11 pages.

*Primary Examiner* — Rex R Holmes
(74) *Attorney, Agent, or Firm* — Faegre Baker Daniels LLP

(57) ABSTRACT

An implantable lead includes a flexible lead body, a plurality of conductor wires and a plurality of electrodes. The implantable lead also includes a terminal connector assembly coupled with a proximal end of the lead body. The terminal connector assembly is sized to be inserted into and received by a connector port of a pulse generator header. The terminal connector assembly includes a plurality of axially spaced terminal ring elements each electrically coupled to at least one of the conductor wires. The terminal ring elements are separated from one another by an electrically insulating material. Each of the terminal ring elements includes an outer surface having a first portion and a second portion, the first portion being electrically conductive and the second portion being electrically non-conductive.

19 Claims, 5 Drawing Sheets

(51) Int. Cl.
*H01R 13/642* (2006.01)
*A61N 1/39* (2006.01)
*H01R 13/17* (2006.01)

(56) References Cited

U.S. PATENT DOCUMENTS

| | | |
|---|---|---|
| 6,895,276 B2 | 5/2005 | Kast et al. |
| 6,895,277 B2 * | 5/2005 | Westlund et al. ............... 607/37 |
| 7,083,474 B1 | 8/2006 | Fleck et al. |
| 7,110,827 B2 | 9/2006 | Sage et al. |
| 7,914,351 B2 | 3/2011 | Balsells et al. |
| 2004/0068303 A1 | 4/2004 | Ostroff |
| 2008/0246231 A1 | 10/2008 | Sjostedt et al. |
| 2008/0319503 A1 | 12/2008 | Honeck et al. |
| 2011/0059639 A1 | 3/2011 | Dilmaghanian et al. |
| 2011/0159748 A1 | 6/2011 | Lim et al. |

* cited by examiner

TERMINAL RING CONFIGURATION TO PREVENT IMPROPER IS4 LEAD CONNECTOR ELECTRICAL CONTACT WITH DF4 CONNECTOR PORT

CROSS-REFERENCE TO RELATED APPLICATIONS

This application claims the benefit under 35 U.S.C. section 119(e) to U.S. provisional application No. 61/715,046 entitled "TERMINAL RING CONFIGURATION TO PREVENT IMPROPER IS4 LEAD CONNECTOR ELECTRICAL CONTACT WITH DF4 CONNECTOR PORT", filed on Oct. 17, 2012, which is herein incorporated by reference in its entirety.

TECHNICAL FIELD

The present invention relates to an implantable system having an implantable lead having a connector port. More specifically, the invention relates to an implantable lead that is configured to comply with the IS4 standard and a connector port that is configured to comply with the DF4 standard.

BACKGROUND

Implantable medical systems for stimulating a target nerve or for diagnostic purposes are well known in the art. Such a system typically includes an implantable lead assembly and an implantable pulse generator connected with the implantable lead assembly. Typically, the implantable lead assembly complies with one or more of the IS-1, IS4, and DF4 standards. Further, a header of the implantable pulse generator generally includes corresponding connector ports that are configured to comply with one or more of the IS-1, IS4, and DF4 standards so that the implantable lead assembly may be effectively coupled with the implantable pulse generator. A proper connection between the implantable leads and the corresponding connector ports is required to allow proper functioning of the implantable system. If a lead assembly compliant with one standard is somehow coupled to a connector port compliant with a different standard, the system will not function properly.

SUMMARY

Example 1 describes an implantable lead configured to be coupled to an implantable pulse generator header having a connector port including a plurality of axially-spaced header contact elements. The implantable lead can include a flexible lead body having a proximal end portion, a distal end portion, and a plurality of conductor lumens extending axially within the lead body from the proximal end to the distal end portion. The implantable lead also includes a plurality of conductor wires, each conductor wire extending within one of the conductor lumens in the lead body. The implantable lead further includes a plurality of electrodes coupled to the lead body in the distal end portion thereof. Each of the electrodes is electrically coupled to at least one of the plurality of conductor wires. The implantable lead also includes a terminal connector assembly coupled to the proximal end of the lead body. The terminal connector assembly is sized to be inserted into and received by the connector port of the pulse generator header. The terminal connector assembly includes a plurality of axially spaced terminal ring elements that each are electrically coupled to at least one of the conductor wires. The terminal ring elements are separated from one another by an electrically insulating material. Each of the terminal ring elements includes an outer surface having a first portion and a second portion. The first portion is electrically conductive and the second portion is electrically non-conductive.

Example 2 is the implantable lead of Example 1, wherein each of the terminal ring elements has a substantially constant outer diameter along its entire axial length.

Example 3 is the implantable lead of Examples 1 and 2, wherein the connector assembly is configured to comply with the IS4 standard.

Example 4 is the implantable lead of Examples 1-3, wherein each of the terminal ring elements includes an electrically conductive terminal ring body having a first axial portion having a first diameter, and a second axial portion having a second diameter equal to or less than the first diameter. The first axial portion defines the electrically conductive first portion of the outer surface of the terminal connector assembly. Each of the terminal ring elements further includes an insulating element disposed about the second axial portion of the terminal ring body. The insulating element defines the electrically non-conductive second portion of the outer surface of the terminal connector assembly.

Example 5 is the implantable lead of Examples 1-4, wherein the second axial portion of the terminal ring body is configured to enhance adhesion between the second axial portion and the insulating element disposed thereabout.

Example 6 is the implantable lead of Example 1-5, wherein the second axial portion of the terminal ring body includes a textured surface configured to enhance adhesion between the second axial portion and the insulating element disposed thereabout.

Example 7 is the implantable lead of Examples 1-6, wherein the second axial portion of the terminal ring body includes a plurality of radial through holes, and wherein the insulating element is configured to interlock with the through holes to enhance adhesion between the second axial portion and the insulating element disposed thereabout.

Example 8 describes a terminal connector assembly for an implantable lead configured to be coupled to an implantable pulse generator header having a connector port including a plurality of axially-spaced header contact elements. The terminal connector assembly is sized to be inserted into and received by the connector port of the pulse generator header. The terminal connector assembly includes a plurality of axially spaced terminal ring elements each electrically coupled to at least one conductor wire of the implantable lead. The terminal ring elements are separated from one another by an electrically insulating material. Each of the terminal ring elements includes an outer surface having a first portion and a second portion. The first portion is electrically conductive and the second portion is electrically non-conductive.

Example 9 is the terminal connector assembly of Example 8, wherein each of the terminal ring elements has a substantially constant outer diameter along its entire axial length.

Example 10 is the terminal connector assembly of Examples 8 and 9, wherein the connector assembly is configured to comply with the IS4 standard.

Example 11 is the terminal connector assembly of Examples 8-10, wherein each of the terminal ring elements includes an electrically conductive terminal ring body having a first axial portion having a first diameter, and a second axial portion having a second diameter equal to or less than the first diameter. The first axial portion defines the electrically conductive first portion of the outer surface of the terminal connector assembly. Each of the terminal ring elements also includes an insulating element disposed about the second axial portion of the terminal ring body. The insulating element defines the electrically non-conductive second portion of the outer surface of the terminal connector assembly.

Example 12 is the terminal connector assembly of Examples 8-11, wherein the second axial portion of the terminal ring body is configured to enhance adhesion between the second axial portion and the insulating element disposed thereabout.

Example 13 is the terminal connector assembly of Examples 8-12, wherein the second axial portion of the terminal ring body includes a textured surface configured to enhance adhesion between the second axial portion and the insulating element disposed thereabout.

Example 14 is the terminal connector assembly of Examples 8-13, wherein the second axial portion of the terminal ring body includes a plurality of radial through holes, and wherein the insulating element is configured to interlock with the through holes to enhance adhesion between the second axial portion and the insulating element disposed thereabout.

Example 15 describes an implantable medical device assembly having an implantable pulse generator. The implantable pulse generator includes a header having a first connector port including a plurality of axially-spaced first header contact elements arranged in a first configuration, and a second connector port including a plurality of axially-spaced second header contact elements arranged in a second configuration. The implantable medical device assembly also includes an implantable lead. The implantable lead includes a flexible lead body having a proximal end portion, a distal end portion, and a plurality of conductor lumens extending axially within the lead body from the proximal end portion to the distal end portion. The implantable lead also includes a plurality of conductor wires, each conductor wire extending within one of the conductor lumens in the lead body. The implantable lead further includes a plurality of electrodes coupled to the lead body in the distal end portion thereof. Each of the electrodes is electrically coupled to at least one of the plurality of conductor wires. The implantable lead also includes a terminal connector assembly coupled to the proximal end of the lead body. The terminal connector assembly is sized to be inserted into and received by the first and second connector ports of the pulse generator header. The terminal connector assembly includes a plurality of axially spaced terminal ring elements that each are electrically coupled to at least one of the conductor wires. The terminal ring elements are separated from one another by an electrically insulating material. Each of the terminal ring elements includes an outer surface having a first portion and a second portion. The first portion is electrically conductive and the second portion is electrically non-conductive. The plurality of ring elements are axially arranged such that upon full insertion of the terminal connector assembly into the first connector port, the first portion of each of the plurality of terminal ring elements is axially aligned with a respective one of the first header contact elements. Alternatively, upon full insertion of the terminal connector assembly into the second connector port, the second portion of each of the plurality of terminal ring elements is axially aligned with a respective one of the second header contact elements and the first portion of each of the terminal ring elements is axially separated and electrically isolated from the respective one of the second header contact elements.

Example 16 is the implantable medical device assembly of Example 15, wherein each of the terminal ring elements has a substantially constant outer diameter along its entire length.

Example 17 is the implantable medical device assembly of Examples 15 and 16, wherein the connector assembly is configured to comply with the 1S4 standard.

Example 18 is the implantable medical device assembly of Examples 15-17, wherein the first connector port is configured to comply with the 1S4 standard, and wherein the second connector port is configured to comply with the DF4 standard.

Example 19 is the implantable medical device assembly of Examples 15-18, wherein each of the terminal ring elements includes an electrically conductive terminal ring body having a first axial portion having a first diameter, and a second axial portion having a second diameter equal to or less than the first diameter. The first axial portion defines the electrically conductive first portion of the outer surface of the terminal connector assembly. Each of the terminal ring elements also includes an insulating element disposed about the second axial portion of the terminal ring body. The insulating element defines the electrically non-conductive second portion of the outer surface of the terminal connector assembly.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
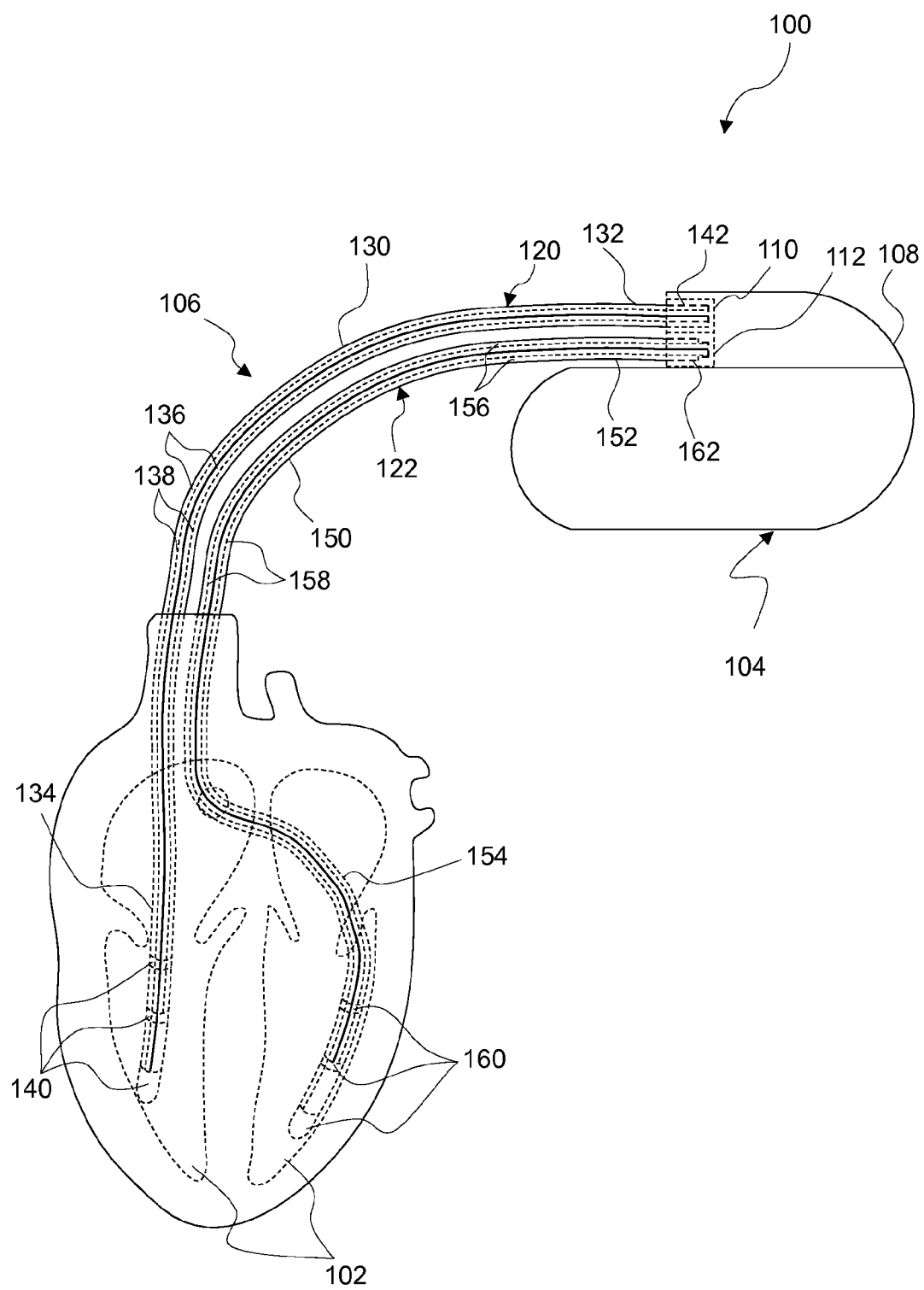
FIG. 1 is a schematic illustration of an implantable system having an implantable lead assembly and an implantable medical device (IMD) in an implanted state, according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic illustration of an implantable system 100 for stimulating a target location 102 on or within the heart. As shown, the system 100 includes an implantable medical device (IMD) 104 and an implantable lead assembly 106 connected to the IMD 104. In various embodiments, the IMD 104 is an implantable pulse generator adapted to generate electrical signals to be delivered to the target location 102 for pacing and/or for sensing electrical activity at a location on or within the heart.

The IMD or pulse generator 104 includes a header 108 having a first connector port 110 and a second connector port 112. The implantable lead assembly 106 includes a first implantable lead 120 connected to the first connector port 110 and a second implantable lead 122 connected to the second connector port 112. In the illustrated embodiment, the first implantable lead 120 is configured to comply with the IS4 standard (low voltage) and the second implantable lead 122 is configured to comply with the DF4 standard (high voltage). Similarly, the first connector port 110 is configured to comply with the IS4 standard and the second connector port 112 is configured to comply with the DF4 standard. In some embodiments, the implantable lead assembly 106 may also include a third implantable lead (not shown) and the header 108 may include a corresponding third connector port (not shown). In certain embodiments, the third implantable lead and the third connector port may be configured to comply with the IS-1 (low voltage) standard.

Each of the first and second implantable leads 120, 122 includes a flexible lead body, a plurality of conductor wires, a plurality of electrodes, and a terminal connector assembly. For example, as shown, the first implantable lead 120 includes a flexible lead body 130 having a proximal end 132, a distal end portion 134, and a plurality of conductor lumens 136 extending axially within the lead body 130 from the proximal end 132 to the distal end portion 134. The first implantable lead 120 also includes a plurality of conductor wires 138, each conductor wire extending within one of the conductor lumens 136 in the lead body 130. The first implantable lead 120 further includes a plurality of electrodes 140 coupled to the distal end portion 134 of the lead body 130. Each of the electrodes 140 is electrically coupled to at least one of the plurality of conductor wires 138. The first implantable lead 120 also includes a terminal connector assembly 142 coupled to the proximal end 132 of the lead body 130. The terminal connector assembly 142 is sized to be inserted into and received by the first connector port 110 of the header 108.

Similarly, the second implantable lead 122 includes a flexible lead body 150 having a proximal end 152, a distal end portion 154, and a plurality of conductor lumens 156 extending axially within the lead body 150 from the proximal end 152 to the distal end portion 154. The second implantable lead 122 also includes a plurality of conductor wires 158, each conductor wire extending within one of the conductor lumens 156 in the lead body 150. Further, the second implantable lead 122 includes a plurality of electrodes 160 coupled to the distal end portion 154 of the lead body 150. Each of the electrodes 160 is electrically coupled to at least one of the plurality of conductor wires 158. The second implantable lead 122 also includes a terminal connector assembly 162 coupled to the proximal end 152 of the lead body 150. The terminal connector assembly 162 is sized to be inserted into and received by the second connector port 112 of the header 108.

As further shown in FIG. 1, the first implantable lead 120 extends into a right ventricle of the heart, and the second implantable lead 122 extends through the coronary sinus and into a coronary vein disposed outside the left ventricle of the heart. The electrical signals and stimuli conveyed by the pulse generator 104 are carried to the electrode at the distal end of lead by the conductors. The pulse generator 104 is typically implanted subcutaneously within an implantation location or pocket in the patient's chest or abdomen.

Figure 2A:
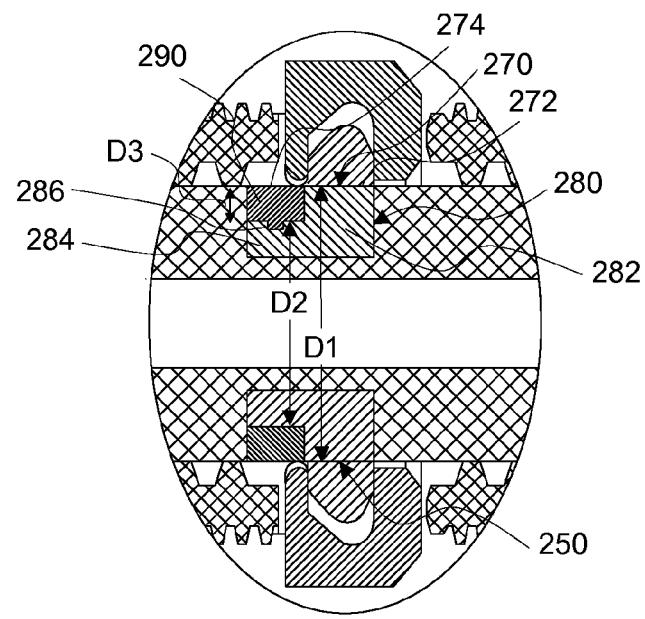
FIG. 2A is an enlarged view of a portion of the header of FIG. 2 depicting a terminal connector assembly, according to an embodiment of the present invention.
Figure 2:
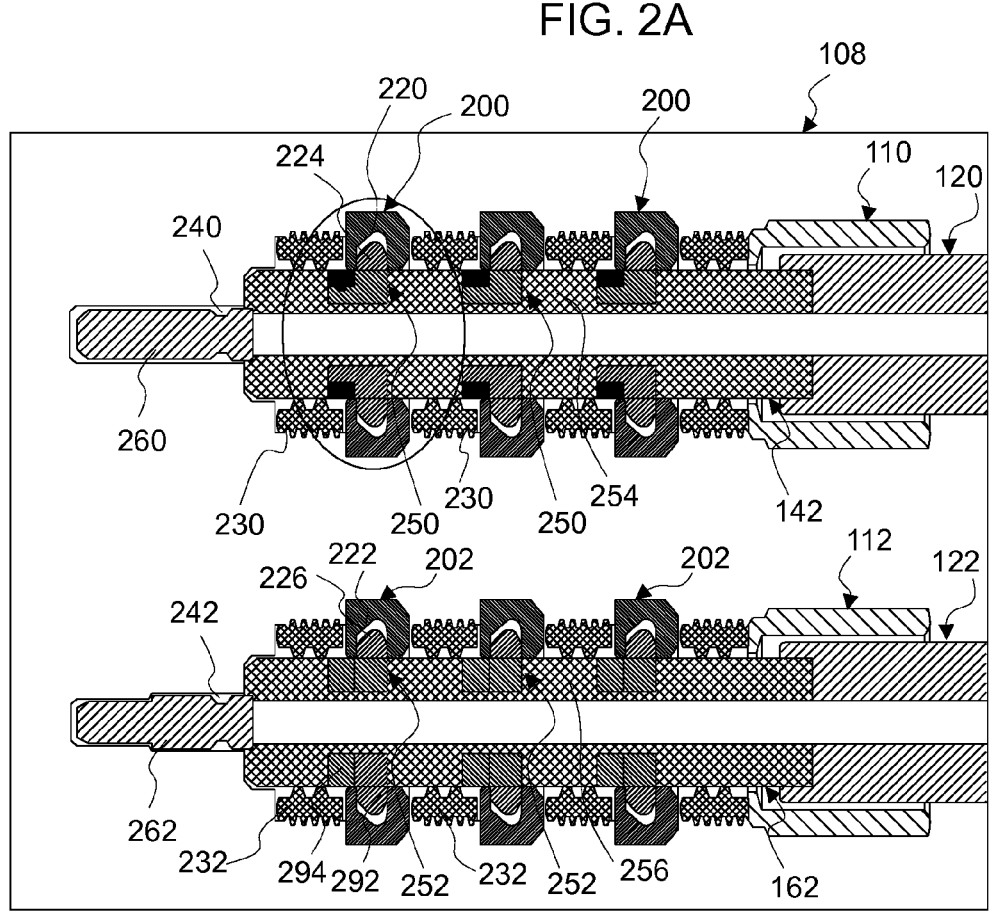
FIG. 2 is a cross-sectional view of a header of the IMD depicting connector ports and implantable leads having proper connection there-between, according to an embodiment of the present invention.

FIG. 2 shows a cross-sectional view of the header 108 with the first and second implantable leads 120, 122 properly connected to the respective first and second connector ports 110, 112. As shown, the first and second connector ports 110,112 include a plurality of axially-spaced first header contact elements 200 and second header contact elements 202, respectively. The header contact elements 200, 202 are made of an electrically conductive material. Each of the first header contact elements 200 includes an intermediate indented portion 220 adapted to receive an electrically conductive flexible ring 224 therein. Similarly, each of the second header contact elements 202 includes an intermediate indented portion 222 adapted to receive electrically conductive flexible rings 226 therein. The electrically conductive flexible rings 224, 226 provide electrical connections to the header contact elements 200, 202 and are sufficiently flexible to facilitate insertion of the leads 120, 122.

The first and second connector ports 110,112 also include insulating members 230 and 232, respectively. The insulating members 230 are disposed between each of the first header contact elements 200, and the insulating members 232 are disposed between each of the second header contact elements 202. The insulating members 230, 232 are made of an electrically non-conductive material. In some embodiments, the first connector port 110 includes a tip cavity 240, and the second connector port 112 includes a tip cavity 242. The tip cavity 240 can be a substantially cylindrical cavity defining a first configuration of the first connector port 110, and the tip cavity 242 can be a stepped cylindrical cavity defining a second configuration of the second connector port 112. The tip cavities 240, 242 of the first and second connector ports 110, 112 can provide a fail-safe feature to the first and second connector ports 110,112, explained in greater detail herein.

As shown in FIG. 2, each of the first and second implantable leads 120, 122 includes terminal connector assemblies 142, 162. Each of the terminal connector assemblies 142, 162 include a plurality of axially spaced terminal ring elements. For example, the terminal connector assembly 142 includes a plurality of axially spaced terminal ring elements 250, and the terminal connector assembly 162 includes a plurality of axially spaced terminal ring elements 252. As discussed herein, each of the plurality of terminal ring elements 250 is electrically coupled to at least one of the conductor wires 138 (e.g., shown in FIG. 1). Similarly, each of the plurality of terminal ring elements 252 is electrically coupled to at least one of the conductor wires 158 (e.g., shown in FIG. 1).

In some embodiments, the terminal ring elements 250, 252 can be separated from one another by an electrically insulating material. As shown, the plurality of terminal ring elements 250 are separated by an electrically insulating material 254, and the plurality of terminal ring elements 252 are separated by an electrically insulating material 256. In one embodiment, the electrically insulating materials 254, 256 can be elongated tubular structures having a plurality of axially spaced peripheral slots for receiving the terminal ring elements 250, 252, respectively, therein.

The terminal connector assemblies 142, 162 can also exhibit a first configuration and a second configuration. For example, the first and second configurations of the terminal connector assemblies 142, 162 are defined by terminal tips 260 and 262, respectively. Similarly to the description of the tip cavities 240, 242 discussed herein, the terminal tip 260 can have a substantially cylindrical structure and the terminal tip 262 can have a stepped cylindrical structure. The terminal tips 260 and 262 are made of electrically conductive material. As such, the terminal tips 260, 262 are configured to conform to the tip cavities 240, 242, of the first and second connector ports 110, 112. As shown, the terminal tips 260, 262 are fully received by the tip cavities 240, 242, thereby allowing full insertion of the first and second implantable leads 120, 122 into the first and second connector ports 110, 112. This establishes a proper connection between the first and second implantable leads 120, 122 with the corresponding first and second connector ports 110, 112.

FIG. 2A shows an enlarged view of the header 108 of the terminal ring elements 250 of the terminal connector assembly 142 shown in FIG. 2. As shown, the terminal ring element 250 includes an outer surface 270 having a first portion 272 and a second portion 274. The first portion 272 is electrically conductive and the second portion is electrically non-conductive. In the present embodiment, the terminal ring element 250 includes an electrically conductive terminal ring body 280. The terminal ring body 280 includes a first axial portion 282 having a first diameter D1, and a second axial portion 284 having a second diameter D2 less than the first diameter D1. The first axial portion 282 defines the electrically conductive first portion 272 of the outer surface 270 of the terminal ring element 250. The primary function of the first axial portion 282 is to receive and transmit electrical signals generated by the IMD 104. The first axial portion 282 is a pristine zone having an annular outer surface. The first axial portion 282 is configured to include a minimum length that complies with ISO 27186:2010 standard. The primary function of the second axial portion 284 is to facilitate in mounting the terminal ring element 250 on the proximal end portion 132 of the lead body 130.

As further shown in FIG. 2A, the terminal ring element 250 also includes an insulating element 290 disposed about the second axial portion 284 of the terminal ring body 280. The insulating element 290 defines the electrically non-conductive second portion 274 of the outer surface 270 of the terminal ring body 280. The terminal ring element 250 includes a substantially constant outer diameter along its entire axial length. Specifically, the insulating element 290 includes a thickness D3, such that when the insulating element 290 is disposed on the second axial portion 284, an outer surface (i.e. the second portion 274 of the outer surface 270) of the insulating element 290 conforms to an outer surface (i.e. the first portion 272 of the outer surface 270) of the first axial portion 282. The insulating element 290 in the present embodiment is shown to cover the processing feature 286. In some embodiments, the insulating element 290 can be formed of an electrically non-conductive polymeric material such as styrene isoprene butadiene (SIBS), polytetrafluoroethylene (PTFE), polyethylene (PE), polypropylene (PP), fluorinated ethylene propylene (FEP), ethylene-tetrafluoroethylene (ETFE), Tecothane, parylene or another biocompatible polymer. In some embodiments, the insulating element 290 may include a ceramic material. In some embodiments, the insulating element 290 may be integrally formed with the lead body or may be a discrete element or component. Further, the insulating element 290 is adapted to be disposed on the second axial portion 284 using various methods that may include but not limited to an over-molding process, a secondary molding, spray coating, chemical vapor deposition and mechanical assembly.

Figure 4A:
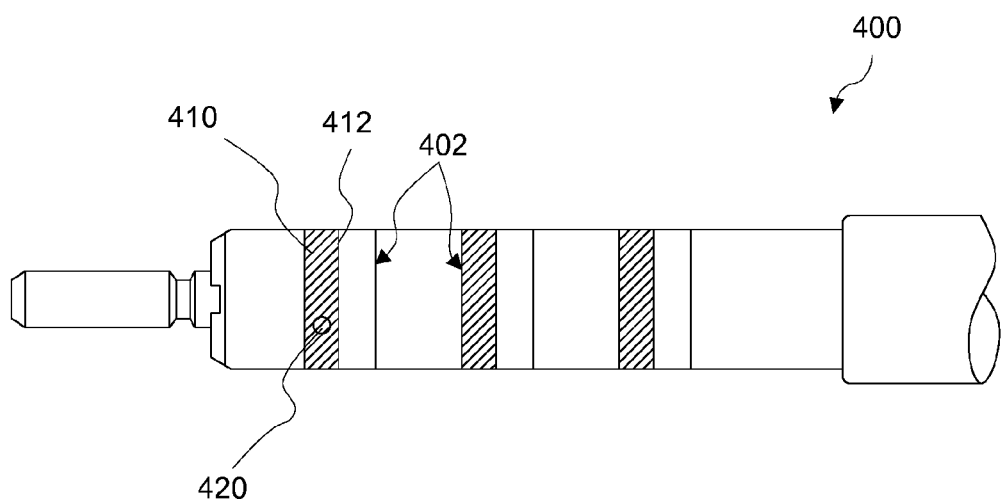
FIGS. 4A-4C illustrate side views of terminal connector assemblies including processing features, according to various embodiments of the present invention.
Figure 4B:
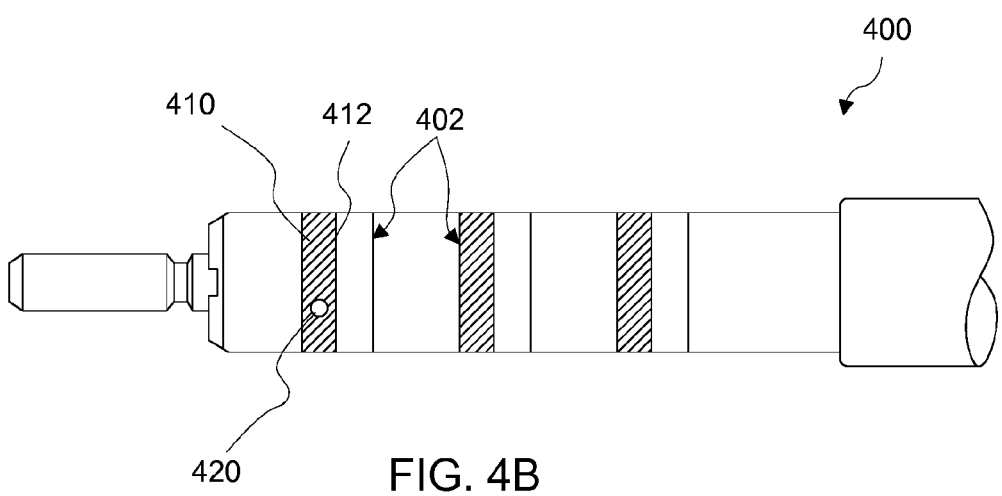
Figure 4C:
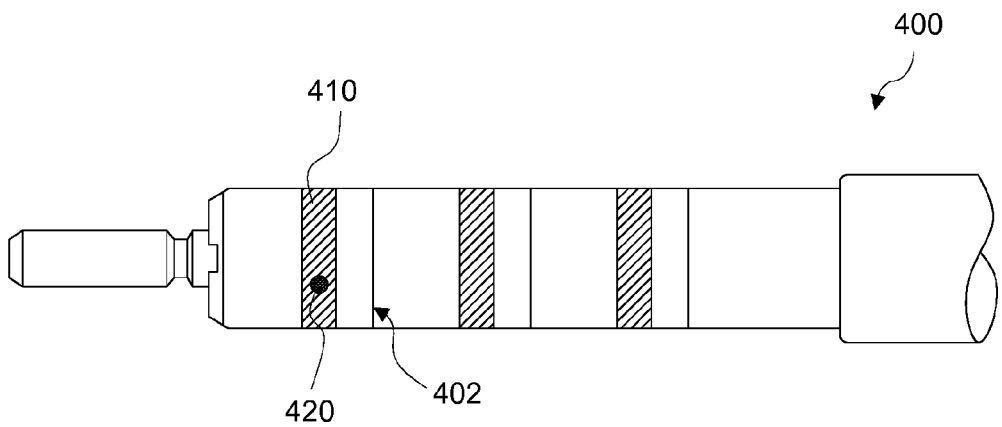

In various embodiments, the second axial portion 284 can include processing features that facilitate downstream manufacturing processes, discussed further herein with respect to FIGS. 4A-4C. In some embodiments, the processing features are configured to be through holes or circular recesses. As shown, the second axial portion 284 includes a processing feature 286 configured as a circular recess and the insulating element 290 includes a protrusion adapted to mate or interlock with the circular recess, such that the insulating element 290 is secured or coupled to the second axial portion 284. In other embodiments, the second axial portion 284 includes a textured surface configured to enhance adhesion or coupling between the second axial portion 284 and the insulating element 290.

As shown in FIG. 2, similarly as discussed with respect to terminal ring elements 250 in FIG. 2A, each of the terminal ring elements 252 can also include electrically conductive first and second axial portions. For example, one of the terminal ring elements 252 is shown to include a first axial portion 292 and a second axial portion 294. As shown, the terminal ring elements 250 axially align with the electrically conductive first header contact elements 200 of the first connector port 110. Specifically, the first portion 272 of the outer surface 270 of the terminal ring element 250 axially aligns and contacts (with the help of the electrically conductive flexible ring 224) the intermediate indented portion 220 of the respective header contact elements 200. Further, the insulating element 290 of the terminal ring elements 250 axially align and contact a portion of the respective header contact elements 200. This establishes the electrical connection between the first implantable lead 120 (complying with the IS4 standard) and the first connector port 110 (complying with the IS4 standard). Similarly, the first portion 294 of the respective terminal ring elements 252 axially aligns with and contacts (with the help of the electrically conductive flexible ring 226) the intermediate indented portion 222 of the respective second header contact elements 202. Further, the second portion 292 of the respective terminal ring elements 252 axially aligns with and contacts a portion of the respective second header contact elements 202. This establishes the electrical connection between the second implantable lead 122 (complying with the DF4 standard) and the second connector port 112 (complying with the DF4 standard).

Figure 3:
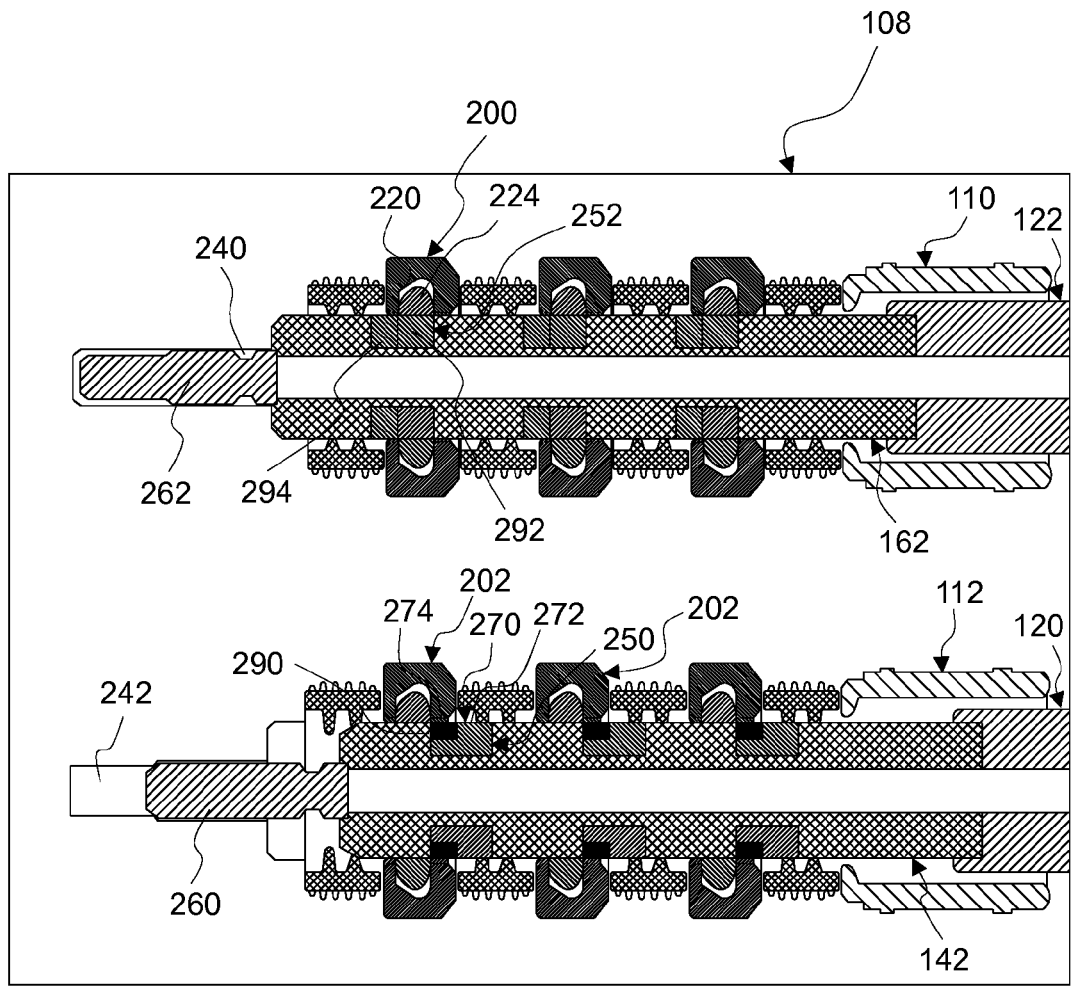
FIG. 3 is a cross-sectional view of the header depicting improper connection between the connector ports and the implantable leads, according to an embodiment of the present invention.

FIG. 3 shows a cross-sectional view of the header 108 with an improper connection between the first and second connector ports 110, 112 and the corresponding first and second implantable leads 120, 122. The improper connection may occur due the substantial structural similarity between the first and second implantable leads 120, 122, and due to the manual insertion of the first and second implantable leads 120, 122 incorrectly into the first and second connector ports 110, 112.

In the embodiment shown, the first connector port 110 fully receives the second implantable lead 122 therein. Specifically, the tip cavity 240 (e.g., substantially cylindrical cavity) fully receives the terminal tip 262 (stepped cylindrical structure) of the terminal connector assembly 162. In this instance, the first portion 294 of the respective terminal ring elements 252 axially aligns with and contacts (with the help of the electrically conductive flexible ring 224) the intermediate indented portion 220 of the respective first header contact elements 200. Further, the second portion 294 of the respective terminal ring elements 252 axially aligns with and contacts a portion of the first header contact elements 200. This establishes an improper connection between the first connector port 110 (complying with the IS4 standard), and the second implantable lead 122 (complying with the DF4 standard). Although the first connector port 110 is improperly connected with the second implantable lead 122, there is no potential damage due to the high voltage nature of the second implantable lead 122 and the low voltage nature of the first connector port 110.

Further, as shown in FIG. 3, the second connector port 112 partially receives the first implantable lead 120 therein. Specifically, the tip cavities 242 (stepped cylinder cavity) partially receives the terminal tip 260 (substantially cylindrical structure) of the terminal connector assembly 142. In such instance, the first portion 272 of the outer surface 270 of the terminal ring element 250 is axially separated from the respective second header contact elements 202. Further, the second portion 274, particularly, the insulating element 290 of the terminal ring element 250 is axially aligned with a portion of the respective second header contact elements 202. The insulating element 290 therefore electrically isolates the terminal ring element 250 from the respective second header contact element 202. Accordingly, the insulating element 290 facilitates in preventing damage that may otherwise occur due to improper connection between the first implantable lead 120 (complying with the IS4 standard) and the second connector port 112 (complying with the DF4 standard). Specifically, the electrical isolation provided by the insulating element 290 avoids delivery of a high voltage shock through the low voltage first implantable lead 120 when connected to the high voltage second connector port 112.

FIGS. 4A-4C show various embodiments of a terminal connector assembly 400 including processing features used in a downstream manufacturing process of an implantable lead, such as the first implantable lead 120 (complying with IS4 standard). FIG. 4A illustrates a side view of the terminal connector assembly 400 having a plurality of terminal ring elements 402 similar to the terminal ring element 250 discussed herein. The terminal connector assembly 400 can also include an insulating element 410 disposed about a second axial portion 412 of the terminal ring element 402. In some embodiments, the insulating element 410 completely covers a processing feature 420 of the terminal ring element 402. Specifically, the processing feature 420, which may be a radial through-hole or a circular recess, is filled with a material of the insulating element 410.

FIG. 4B shows a side view of the terminal connector assembly 400 having the insulating element 410 partially disposed on the second axial portion 412 of the terminal ring elements 402. The insulating element 410 partially covers the second axial portion 412 such that the processing feature 420 remains exposed. FIG. 4C shows a side view of the terminal connector assembly 400 with the processing feature 420 being covered by a same or different insulating material as that of the insulating element 410.

Figure 5:
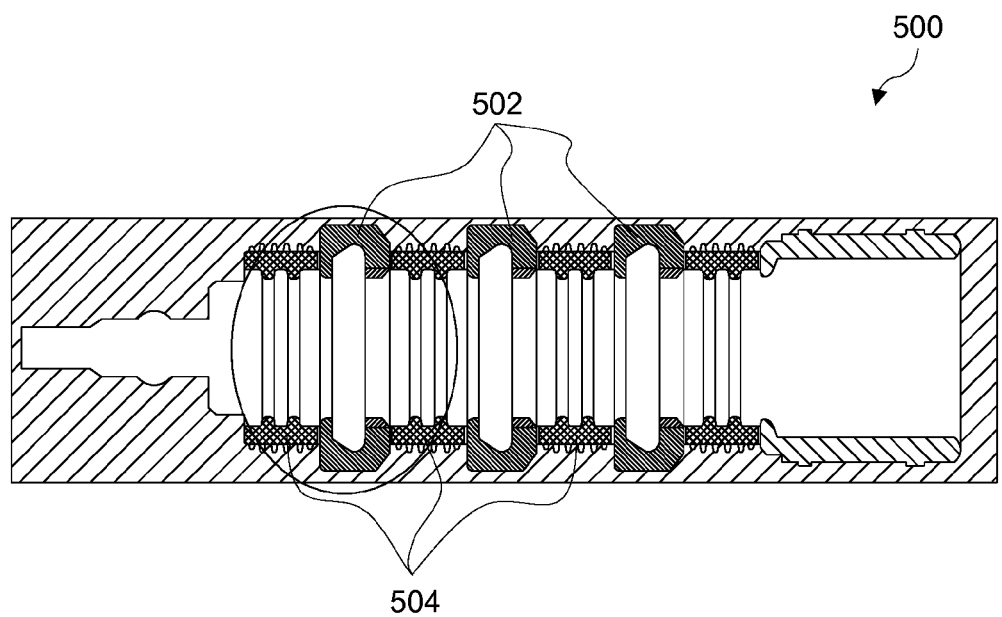
FIG. 5 illustrates a cross-sectional view of a connector port of a header of an IMD, according to an alternative embodiment of the present invention.

FIG. 5 shows a cross-sectional view of a connector port 500 according to an embodiment. As shown, the connector port 500 is configured to comply with the DF4 standard, and adapted to prevent a situation where a high voltage shock is delivered through an IS4 implantable lead when connected to the connector port 500. The connector port 500 includes a plurality of axially-spaced header contact elements 502. The connector port 500 also includes insulating members 504 disposed between each of the plurality of header contact elements 502.

Figure 5A:
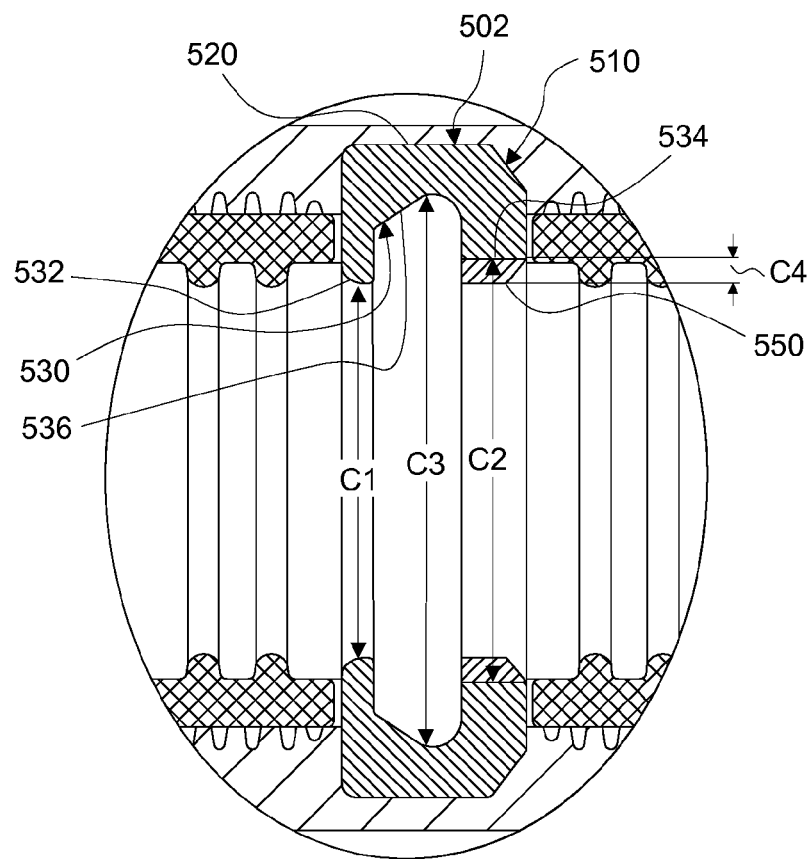
FIG. 5A illustrates enlarged view of a portion of the header of FIG. 5 depicting header contact elements of the connector port, according to an embodiment of the present invention.

FIG. 5A shows an enlarged view of a portion of the connector port 500. Specifically, one of the header contact element 502 is shown to include an electrically conductive portion and an electrically non-conductive portion. For example, the header contact element 502 includes a conductive portion 510 having an outer surface 520 and an inner surface 530. The inner surface 530 includes a proximal portion 532 having a first diameter C1, a distal portion 534 having a second diameter C2 more than the first diameter C1, and an intermediate indented portion 536 between the proximal portion 532 and the distal portion 534. The intermediate indented portion 536 includes a third diameter C3 more than the first and second diameters C1, C2.

The header contact element 502 includes a non-conductive portion 550. The non-conductive portion 550 is generally a ring shaped structure made of electrically non-conductive material that can be disposed about the distal portion 534 of the inner surface 530. The non-conductive portion 550 includes a thickness C4 such that an inner diameter of the non-conductive portion 550 conforms to the first diameter C1 of the proximal portion 532. Further, the thickness C4 of the non-conductive portion 550 is configured to comply with the ISO 27186:2010 standard.

In operation, the connector port 500 may receive a terminal connector assembly of an implantable lead (not shown) complying with the IS4 standard, therein, to establish an improper connection there-between. The non-conductive portion 550 electrically isolates the conductive portion 510 of the header contact element 502 from the lead which is conductive in nature at least at the contact area. This prevents a situation where a high voltage shock is being delivered from the connector port 500 (complying with the DF4 standard) through the implantable lead (complying with the DF4 standard).

The above discussion suggests that the non-conductive portion 550 is disposed about the distal portion 534 of the inner surface 530 of the conductive portion 510. In some alternative embodiments, a non-conductive portion can be disposed adjacent a conductive portion sidewise. For example, a header contact element can include an electrically conductive proximal end portion and an electrically conductive intermediate indented portion integral with the proximal end portion. The header contact element can also include an electrically non-conductive distal end portion coupled to the intermediate indented portion. In some embodiments, the distal end portion can be coupled to the intermediate indented portion by a variety of different techniques, including a snap-fit arrangement, a threadable arrangement, a press-fit arrangement or a sweat-fit arrangement.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as falling within the scope of the claims, together with all equivalents thereof.

We claim:

1. An implantable lead configured to be coupled to an implantable pulse generator header having a connector port including a plurality of axially-spaced header contact elements, the lead comprising:
   a flexible lead body having a proximal end, a distal end portion, and a plurality of conductor lumens extending axially within the lead body from the proximal end to the distal end portion;
   a plurality of conductor wires, each conductor wire extending within one of the conductor lumens in the lead body;
   a plurality of electrodes coupled to the lead body in the distal end portion thereof, each of the electrodes being electrically coupled to at least one of the plurality of conductor wires; and
   a terminal connector assembly coupled to the proximal end of the lead body, the terminal connector assembly sized to be inserted into and received by the connector port of the pulse generator header and including a plurality of axially spaced terminal ring elements each electrically coupled to at least one of the conductor wires, the terminal ring elements separated from one another by an electrically insulating material having an outer surface, the terminal ring elements each having an outer surface aligned with the outer surface of the electrically insulating material and having a first portion and a second portion, the first portion being electrically conductive and the second portion being electrically non-conductive, and a plurality of electrically conductive flexible rings, the electrically conductive flexible rings each being arranged on the outer surface of the terminal ring elements at the first portion and configured to provide electrical connections to the pulse generator header.

2. The implantable lead of claim 1, wherein each of the terminal ring elements has a substantially constant outer diameter along its entire axial length.

3. The implantable lead of claim 1, wherein the connector assembly is configured to comply with IS4 standards.

4. The implantable lead of claim 1, wherein each of the terminal ring elements includes:
  an electrically conductive terminal ring body having a first axial portion having a first diameter, and a second axial portion having a second diameter equal to or less than the first diameter, the first axial portion defining the electrically conductive first portion of the outer surface of the terminal connector assembly; and
  an insulating element disposed about the second axial portion of the terminal ring body, the insulating element defining the electrically non-conductive second portion of the outer surface of the terminal connector assembly.

5. The implantable lead of claim 4, wherein the second axial portion of the terminal ring body is configured to enhance adhesion between the second axial portion and the insulating element disposed thereabout.

6. The implantable lead of claim 5, wherein the second axial portion of the terminal ring body includes a textured surface configured to enhance adhesion between the second axial portion and the insulating element disposed thereabout.

7. The implantable lead of claim 5, wherein the second axial portion of the terminal ring body includes a plurality of radial through holes, and wherein the insulating element is configured to interlock with the through holes to enhance adhesion between the second axial portion and the insulating element disposed thereabout.

8. A terminal connector assembly for an implantable lead configured to be coupled to an implantable pulse generator header having a connector port including a plurality of axially-spaced header contact elements, the terminal connector assembly sized to be inserted into and received by the connector port of the pulse generator header and comprising a plurality of axially-spaced terminal ring elements each electrically coupled to at least one conductor wire of the implantable lead, the terminal ring elements separated from one another by an electrically insulating material having an outer surf, the terminal ring elements each having an outer surface aligned with the outer surface of the electrically insulating material and having a first portion and a second portion, the first portion being electrically conductive and the second portion being electrically non-conductive, and a plurality of electrically conductive flexible rings, the electrically conductive flexible rings each being arranged on the outer surface of the terminal ring elements at the first portion and configured to provide electrical connections to the pulse generator header.

9. The terminal connector assembly of claim 8, wherein each of the terminal ring elements has a substantially constant outer diameter along its entire axial length.

10. The terminal connector assembly of claim 8, wherein the connector assembly is configured to comply with IS4 standards.

11. The terminal connector assembly of claim 8, wherein each of the terminal ring elements includes:
  an electrically conductive terminal ring body having a first axial portion having a first diameter, and a second axial portion having a second diameter equal to or less than the first diameter, the first axial portion defining the electrically conductive first portion of the outer surface of the terminal connector assembly; and
  an insulating element disposed about the second axial portion of the terminal ring body, the insulating element defining the electrically non-conductive second portion of the outer surface of the terminal connector assembly.

12. The terminal connector assembly of claim 11, wherein the second axial portion of the terminal ring body is configured to enhance adhesion between the second axial portion and the insulating element disposed thereabout.

13. The terminal connector assembly of claim 12, wherein the second axial portion of the terminal ring body includes a textured surface configured to enhance adhesion between the second axial portion and the insulating element disposed thereabout.

14. The terminal connector assembly of claim 12, wherein the second axial portion of the terminal ring body includes a plurality of radial through holes, and wherein the insulating element is configured to interlock with the through holes to enhance adhesion between the second axial portion and the insulating element disposed thereabout.

15. An implantable medical device assembly comprising:
  an implantable pulse generator including a header having a first connector port including a plurality of axially-spaced first header contact elements arranged in a first configuration, and a second connector port including a plurality of axially-spaced second header contact elements arranged in a second configuration; and
  an implantable lead including:
    a flexible lead body having a proximal end, a distal end portion, and a plurality of conductor lumens extending axially within the lead body from the proximal end to the distal end portion;
    a plurality of conductor wires, each conductor wire extending within one of the conductor lumens in the lead body;
    a plurality of electrodes coupled to the lead body in the distal end portion thereof, each of the electrodes being electrically coupled to at least one of the plurality of conductor wires; and
    a terminal connector assembly coupled to the proximal end of the lead body, the terminal connector assembly sized to be inserted into and received by the first and second connector ports of the pulse generator header and including a plurality of axially-spaced terminal ring elements each electrically coupled to at least one of the conductor wires, the terminal ring elements separated from one another by an electrically insulating material having an outer surface, the terminal ring elements each having an outer surface aligned with the outer surface of the electrically insulating material and having a first portion and a second portion, the first portion being electrically conductive and the second portion being electrically non-conductive, and a plurality of electrically conductive flexible rings, the electrically conductive flexible rings each being arranged on the outer surface of the terminal ring elements at the first portion and configured to provide electrical connections to the pulse generator header wherein the plurality of ring elements are axially arranged such that:

upon full insertion of the terminal connector assembly into the first connector port, the first portion of each of the plurality of terminal ring elements is axially aligned with a respective one of the first header contact elements, and upon full insertion of the terminal connector assembly into the second connector port, the second portion of each of the plurality of terminal ring elements is axially aligned with a respective one of the second header contact elements and the first portion of each of the terminal ring elements is axially separated and electrically isolated from the respective one of the second header contact elements.

16. The implantable medical device assembly of claim 15, wherein each of the terminal ring elements has a substantially constant outer diameter along its entire length.

17. The implantable medical device assembly of claim 15, wherein the connector assembly is configured to comply with IS4 standards.

18. The implantable medical device assembly of claim 17, wherein the first connector port is configured to comply with IS4 standards, and wherein the second connector port is configured to comply with DS4 standards.

19. The implantable medical device assembly of claim 17, wherein each of the terminal ring elements includes:

an electrically conductive terminal ring body having a first axial portion having a first diameter, and a second axial portion having a second diameter equal to or less than the first diameter, the first axial portion defining the electrically conductive first portion of the outer surface of the terminal connector assembly; and an insulating element disposed about the second axial portion of the terminal ring body, the insulating element defining the electrically non-conductive second portion of the outer surface of the terminal connector assembly.

\* \* \* \* \*